US012789497B2

(12) United States Patent
Curtis et al.

(10) Patent No.: US 12,789,497 B2
(45) Date of Patent: Nov. 10, 2026

(54) TOOTH WHITENING PRODUCT

(71) Applicant: The Procter & Gamble Company, Cincinnati, OH (US)

(72) Inventors: Michael David Curtis, Mason, OH (US); Franco Silva Medeiros, Loveland, OH (US); Natalia Maria Ramon Martinez, West Chester, OH (US); Jayanth Rajaiah, Loveland, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 991 days.

(21) Appl. No.: 17/410,188

(22) Filed: Aug. 24, 2021

(65) Prior Publication Data

US 2022/0054372 A1 Feb. 24, 2022

Related U.S. Application Data

(60) Provisional application No. 63/069,668, filed on Aug. 24, 2020.

(51) Int. Cl.

| | |
|---|---|
| ***B32B 1/08*** | (2006.01) |
| ***A45D 40/00*** | (2006.01) |
| ***A61J 1/14*** | (2023.01) |
| ***A61K 8/06*** | (2006.01) |
| ***A61K 8/31*** | (2006.01) |
| ***A61Q 11/00*** | (2006.01) |
| ***B32B 1/00*** | (2006.01) |
| ***B32B 27/08*** | (2006.01) |
| ***B32B 27/32*** | (2006.01) |

(52) U.S. Cl.

CPC ................ *B32B 1/08* (2013.01); *A45D 40/00* (2013.01); *A61J 1/1468* (2015.05); *A61K 8/06* (2013.01); *A61K 8/31* (2013.01); *A61Q 11/00* (2013.01); *B32B 1/00* (2013.01); *B32B 27/08* (2013.01); *B32B 27/32* (2013.01); *A61K 2800/87* (2013.01); *B32B 2250/02* (2013.01); *B32B 2250/242* (2013.01); *B32B 2270/00* (2013.01); *B32B 2307/724* (2013.01); *B32B 2439/80* (2013.01)

(58) Field of Classification Search

CPC ....... A61K 8/06; A61K 2800/87; A61Q 11/00

See application file for complete search history.

(56) References Cited

U.S. PATENT DOCUMENTS

| | | | | |
|---|---|---|---|---|
| 4,539,259 | A * | 9/1985 | Zuscik | B32B 27/08 428/347 |
| 4,556,553 | A * | 12/1985 | Suganuma | A61K 8/73 206/524.1 |
| 6,113,885 | A | 9/2000 | Pipes | |
| 8,377,532 | B2 * | 2/2013 | Maurice | B32B 27/32 428/35.8 |
| 9,898,774 | B2 | 2/2018 | Choi | |
| 2004/0241362 | A1 * | 12/2004 | Marechal | B32B 27/08 526/352 |
| 2007/0280894 | A1 | 12/2007 | Romano et al. | |
| 2018/0133502 | A1 * | 5/2018 | Rajaiah | A61K 8/064 |
| 2024/0024214 | A9 | 1/2024 | Rajaiah | |

FOREIGN PATENT DOCUMENTS

| | | | |
|---|---|---|---|
| CN | 201086898 | Y | 7/2008 |
| EP | 0255210 | B1 | 9/1992 |
| EP | 2361604 | A1 | 8/2011 |
| EP | 3315120 | A1 | 5/2018 |
| JP | S6075410 | A | 4/1985 |
| JP | S6075411 | A | 4/1985 |
| JP | H10329850 | A | 12/1998 |
| JP | 2005246878 | A | 9/2005 |

OTHER PUBLICATIONS

PCT Search Report and Written Opinion for PCT/US2021/047239 dated Jan. 7, 2022, 15 pages.

* cited by examiner

*Primary Examiner* — Andrew S Rosenthal

(74) *Attorney, Agent, or Firm* — John G. Powell; Jason Jeffrey Camp

(57) ABSTRACT

A tooth whitening product comprises a multi-phase oral composition contained in a package. The multi-phase composition comprises a hydrophobic phase comprising a flavor, and a hydrophilic phase comprising a peroxide bleaching agent. The package comprises a container formed of an oxygen-permeable substrate comprising one or more layers, wherein the substrate has an oxygen transmission rate at 23° C. of at least about 5 cc/(m2*day) and the substrate is free of a barrier layer. A dispensing orifice in fluid communication with the container is covered by a cap.

24 Claims, 2 Drawing Sheets

TOOTH WHITENING PRODUCT

FIELD OF THE INVENTION

The present invention relates to a tooth whitening product comprising a multi-phase oral composition comprising a hydrophobic phase comprising flavor and a hydrophilic phase comprising a peroxide bleaching agent, wherein the composition is contained in a package comprising an oxygen-permeable substrate.

BACKGROUND OF THE INVENTION

Currently in the marketplace are dental products by which various cosmetic and/or therapeutic actives are delivered to teeth and the oral cavity. Examples of such products include: brushing aids, such as dentifrice products for delivery of oral care actives for example polyphosphates or fluorides; mouthwashes containing breath fresheners or antibacterial actives; and whitening strips for the delivery of bleaching actives to the teeth. In particular, the use of a dental strip has been recognized as a convenient and inexpensive way to deliver cosmetic and therapeutic benefits to the teeth and mucosal surfaces of the oral cavity; for example, dental whitening strips, where a whitening composition is applied to a strip and thereafter applied to the teeth to achieve sustained contact between the teeth and the whitening composition.

Despite the above known approaches for the treatment of oral conditions, especially for the whitening of teeth, a need still exists for providing improved tooth whitening products with enhanced convenience for consumers along with acceptable product storage stability, while preferably providing improved bleaching efficacy, increased speed of whitening, decreased tooth-sensitivity, decreased oral soft tissue irritation. With such products, there is often a tradeoff between maintaining storage stability of certain compositional ingredients, such as flavor, with respect to other compositional ingredients, such as peroxide, when contained in a package. There thus remains a desire for products having enhanced convenience and preference for the consumer, while maintaining stability of the package and composition contained therein.

SUMMARY OF THE INVENTION

Tooth whitening products of the present invention comprise a multi-phase oral composition contained in a package. The multi-phase oral composition comprises a hydrophobic phase comprising a flavor, and a hydrophilic phase comprising a peroxide bleaching agent. The package comprises a container formed of an oxygen-permeable substrate comprising one or more layers. The substrate has an oxygen transmission rate at 23° C. of at least about 5 cc/(m$^2$*day). The oxygen-permeable substrate helps to prevent undesirable expansion of the container due to oxidation of the peroxide during storage, while the hydrophobic phase helps to maintain stability of the flavor contained in the hydrophobic phase.

DETAILED DESCRIPTION OF THE INVENTION

Definitions

Figure 1:
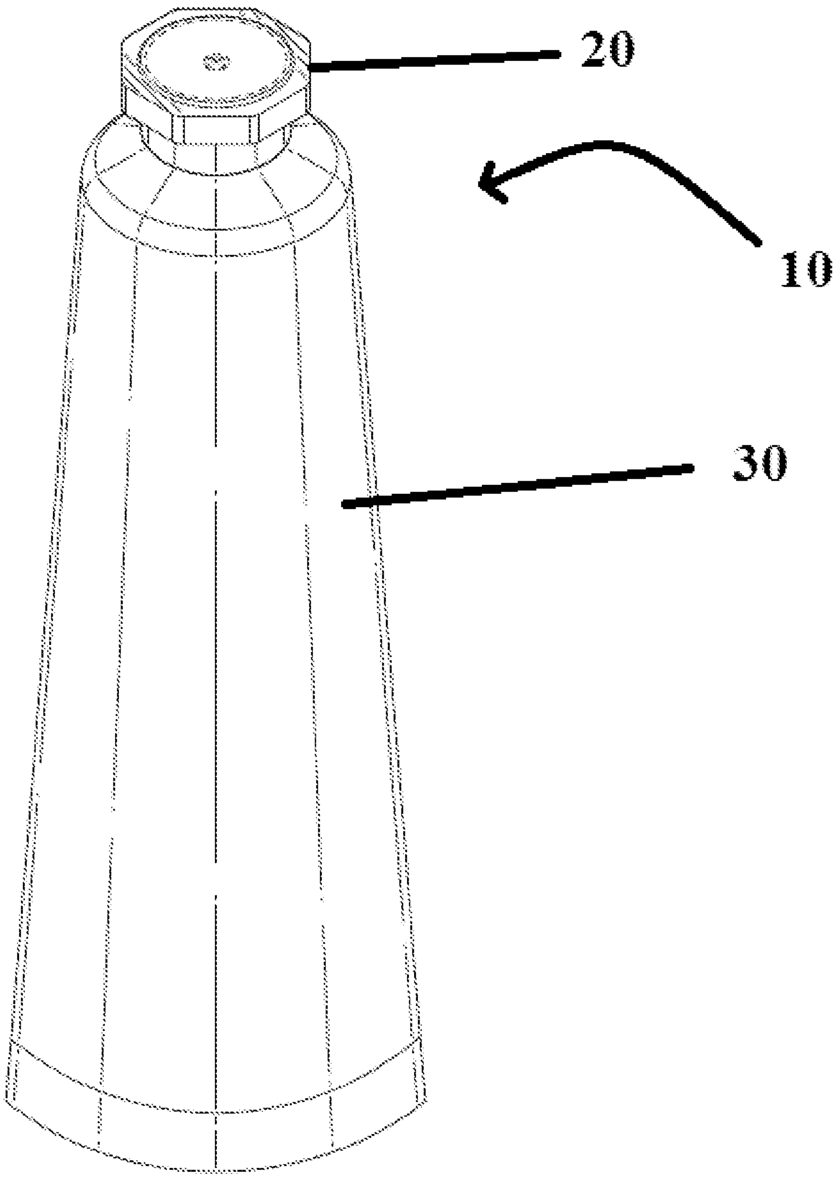
FIG. 1 is a perspective view of a tooth whitening product of the present invention.

The term "phase" as used herein means a physically distinct region or regions, which may be continuous or discontinuous, having one or more properties that are different from another phase. Non-limiting examples of properties that may be different between phases include composition, viscosity, solubility, hydrophobicity, hydrophilicity, and miscibility.

The term "multi-phase oral composition" as used herein comprises a mixture of two or more phases that are immiscible with each other. The phases may be continuous, discontinuous, or combinations thereof. Examples of multi-phase oral compositions include emulsions, such as water in oil emulsions. Examples of multi-phase oral compositions also include oil-in-water emulsions, water-in-oil-in-water emulsions, and oil-in-water-in-oil emulsions. Examples of multi-phase oral compositions also include compositions where the phases are multi-continuous including bi-continuous, layered, striped, marbled, ribbons, swirled, and combinations thereof.

The term "emulsion" as understood herein is an example of a multi-phase composition wherein: 1) at least one of the phases is discontinuous and 2) at least one of the phases is continuous. Examples of emulsions include droplets of water dispersed in oil. In this example the water and oil would be mutually immiscible with each other, water would be the discontinuous phase, and the oil would be the continuous phase.

The term "water-in-oil emulsion" as understood herein is an example of an emulsion wherein 1) the discontinuous phase is aqueous, and 2) the continuous phase is hydrophobic.

The term "aqueous phase" as understood herein is at least one hydrophilic phase that comprises water and an active agent (e.g. bleaching agent), and is immiscible with the hydrophobic phase. In certain embodiments, each part of the aqueous phase contains at least 2% of the active agent by weight of the aqueous phase. Optionally the aqueous phase may further comprise ingredients that are water soluble, water miscible, or combinations thereof, such as for example water soluble solvents, alcohol, polyethylene glycol, carbopol, etc. or mixtures thereof. In some embodiments, if and when immiscible fillers are added to the aqueous phase, the percentage of the aqueous phase in the composition is calculated by excluding the immiscible filler.

The term "hydrophobic phase" as understood herein means all components of the composition that are immiscible with the hydrophilic phase (e.g. aqueous phase). In certain embodiments the hydrophobic phase may further comprise ingredients that are soluble, miscible or combinations thereof in the hydrophobic phase, such as for example hydrocarbon solvents dissolved into the hydrophobic phase, polyethylene dissolved into the hydrophobic phase, microcrystalline wax dissolved into the hydrophobic phase, or mixtures thereof.

The term "particle" as used herein is a discrete, solid or semisolid material. Solid particles have dimensions larger than individual atoms or molecules and are typically submicron to about a millimeter in their largest dimension. In certain embodiments, particles may be agglomerated into an agglomerate of discrete particles. In certain embodiments particles may have dimensions or a number-average equivalent-diameter or volume-average equivalent-diameter from about 50 nm to about 1 mm.

The term "hydrophilic bleaching agent particle" as used herein is a particle that a) comprises a bleaching agent, and b) is soluble in water, swells (increase in volume and/or weight) upon contact with water or releases a bleaching agent upon contact with water. If a bleaching agent is released, the bleaching agent may be a gas, liquid, or solid dissolved in a liquid. In certain embodiments the hydrophilic bleaching agent particle is insoluble in the hydrophobic phase. In certain embodiments the hydrophilic bleaching agent particles or multi-phase oral composition may further comprise ingredients that are water soluble, water miscible, or combinations thereof, such as for example water water-soluble solvents, alcohols, carbopol, polyalkylene glycols, humectants, glycerin, sorbitol, xylitol, butylene glycol, polyethylene glycol, and propylene glycol, and mixtures thereof. In certain embodiments, the hydrophilic bleaching agent particles may also include water of hydration or solvents of crystallization. If these ingredients are added to or present in the hydrophilic bleaching agent particles, the percentage of the hydrophilic bleaching agent particles in the composition is calculated by excluding these ingredients. If water-insoluble or water-immiscible fillers are added to the hydrophilic bleaching agent particles or oral composition, the percentage of the hydrophilic bleaching agent particles in the composition is calculated by excluding these fillers.

Tooth Whitening Product

The tooth whitening product of the present invention is used by consumers to whiten the teeth of the consumer. The product can be conveniently used at home by the consumer. The tooth whitening product comprises a package containing a multi-phase oral composition, as described herein.

Package

The package utilized in the tooth whitening product of the present invention comprises a container formed of an oxygen-permeable substrate comprising one or more layers, wherein the substrate has an oxygen transmission rate at 23° C. of at least about 5 cc/(m2*day), a dispensing orifice in fluid communication with the container, and a cap removably attached to the container and covering the dispensing orifice. The substrate of the container is free of a barrier layer.

Oxygen-Permeable Substrate

The container of the present invention is formed of an oxygen-permeable substrate comprising one or more layers. The layer(s) of the substrate will typically comprise a polyolefin-based material. By "polyolefin-based material" it is to be understood herein that all different types of polyolefins and metallocene resins well known in the art including the polyolefin copolymers having olefinic monomers such as ethylene, propylene, butene, and the like, are suitable. Preferred herein are polyethylenes such as low density polyethylene (LDPE), linear low density polyethylene (LLDPE), high density polyethylene (HDPE), and the like, and combinations thereof. Such polyethylenes are known to those skilled in the art and are commercially available, for example, from Dow Chemical and Shell Petrochemical.

The layer(s) of polyolefin-based material can be blended, laminated (e.g. via adhesive), and/or coextruded together. Preferred herein are laminated or coextruded materials comprising a low density polyethylene, a linear low density polyethylene, a high density polyethylene, or mixtures thereof. The substrates can have different thicknesses and densities depending on their use.

The oxygen-permeable substrate can comprise one layer, two layers, three layers, four layers, or more than four layers. In one aspect, the substrate comprises two layers or three layers.

The oxygen-permeable substrate can have an overall thickness of from about 0.1 mm to about 2 mm, preferably from about 0.2 mm to about 0.6 mm. The thickness of each layer can be from about 0.003 mm to about 1 mm, preferably from about 0.1 mm to about 0.3 mm.

The substrate can be supplied as a sheet of material, which can then be formed into a container using conventional methods. The container can be in a variety of forms, most commonly in the form of a tube. A tube will typically have one end that is sealed, e.g. crimped and/or heat-sealed, and one end having an orifice for dispensing the composition contained in the container. The orifice of the tube is typically covered by a cap, which can be a removable cap (e.g. threaded cap or pull-off cap) or a flip-top cap having a hinge.

The substrate can further comprise colorant, such as dyes or pigments, to impart a desired color to the substrate.

The outer surface of the substrate can be decorated using inks, metallic hot stamping foil, and/or matte or gloss varnishes.

The container formed from the oxygen-permeable substrate can be in a variety of forms, including a tube or bottle, and preferably a tube having a seal at one end of the tube and the dispensing orifice at the opposite end of the tube.

Oxygen Transmission Rate (OTR)

The oxygen-permeable substrate of the present invention has an oxygen transmission rate (OTR) that is suitable to facilitate a sufficient amount of oxygen generated inside the container to diffuse through the substrate to prevent expansion of the container during storage due to oxidation of the peroxide contained in the tooth whitening composition of the present invention. The substrate will therefore have an OTR of at least about 5 cubic centimeters per square meter per day (cc/($m^2$*day)), at least about 10 cc/($m^2$*day), at least about 20 cc/($m^2$*day), at least about 50 cc/($m^2$*day), at least about 100 cc/($m^2$*day), or at least about 200 cc/($m^2$*day). Preferably, the substrate will have an OTR of from about 5 to about 500 cc/($m^2$*day), from about 10 to about 300 cc/($m^2$*day).

The OTR of a sample of the oxygen-permeable substrate is measured according to ASTM D3985 ("Standard Test Method for Oxygen Gas Transmission Rate Through Plastic Film Sheeting Using Coulometric Sensor"). Such an OTR measurement can be made using an Oxtran 2/21 Oxygen Permeability Instrument available from MOCON Laboratory (Minneapolis, Minnesota, USA).

Dispensing Orifice

The dispensing orifice of the container will typically have a minimum diameter of at least about 0.5 mm, preferably at least about 1 mm, preferably at least about 1.5 mm, or preferably at least about 2 mm. The dispensing orifice will preferably have a minimum diameter of from about 0.5 mm to about 10 mm, or preferably from about 1 mm to about 5 mm, or preferably from about 1 mm to about 3 mm. The minimum diameter is the shortest distance measured between two points opposite each other along the perimeter of the orifice. If the orifice is circular, the minimum diameter is the diameter of the circular orifice. The orifice can be in a variety of shapes, including circular, oval, rectangular, star-shaped, and the like.

The minimum diameter of the dispensing orifice can be important depending on the nature of the multi-phase oral composition. For example, when the multi-phase oral composition has a cone penetration consistency value of from about 10 to about 500, or from about 100 to about 300, the dispensing orifice preferably has a minimum diameter of at least about 1 mm, preferably at least about 1.75 mm, and preferably at least about 2 mm.

In one aspect, the dispensing orifice is a ribbon orifice having an oval or rectangular shape. Such a ribbon orifice is described in detail in U.S. application Ser. No. 16/898,471, filed Jun. 11, 2020, which is incorporated by reference herein.

Free of Barrier Layer

The substrate used to form the container of the present invention is free of a barrier layer. Barrier layers are commonly used in cosmetic or toothpaste tubes to better isolate the composition contained within such tubes from the environment to improve stability of the composition during storage. As such, more volatile components of the composition, such as flavors or perfumes, will tend to be more stable, as well as other components that may tend to react with environmental components. Barrier layers will typically have an oxygen transmission rate (OTR) of less than about 5, less than about 4, less than about 3, less than about 2, less than about 1, or less than about 0.5 cc/(m2*day) at 23° C., as measured according to ASTM D3985. Therefore, substrates which contain a barrier layer will therefore have an OTR which is the same as, or less than, the OTR of the barrier layer.

However, when a composition contained within a container having a barrier layer comprises a peroxide material (especially in aqueous form or within an aqueous phase of the composition), the container having a barrier layer can suffer from unacceptable expansion of the container during storage of the composition due to a level of oxidation of the peroxide material over time in storage. This can lead to the container looking unsightly (e.g. bloated) or even leakage of the composition from the container due to failure of seals of the container resulting from the expansion of the container. As such, there is a need to maintain stability of the composition contained within the container while Examples of barrier layers, which are not present in the substrate which forms the container herein, include an aluminum barrier layer (ABL) and a plastic barrier layer (PBL), such as an ethyl vinyl alcohol barrier layer.

Optional Applicator Tip

The package of the present invention can optionally further comprise an applicator tip which comprises the dispensing orifice. In this regard, a separate applicator device is not required to apply the multi-phase oral composition to teeth. A suitable package comprising an applicator tip is described in co-pending U.S. Application Ser. No. 63/069,660, filed Aug. 24, 2020.

Multi-Phase Oral Composition

The multi-phase oral compositions of the present invention comprise a hydrophobic phase and a hydrophilic phase. The multi-phase oral composition is preferably in the form of an emulsion. Examples of multi-phase oral compositions in the form of an emulsion include oil-in-water emulsions, water-in-oil-in-water emulsions, and oil-in-water-in-oil emulsions. The multi-phase oral composition can also include compositions wherein the phases are multi-continuous (including bi-continuous), layered, striped, marbled, ribbons, swirled, and combinations thereof.

Hydrophobic Phase

The hydrophobic phase of the multi-phase oral composition comprises flavor to impart a pleasant taste and/or odor during use of the composition by a consumer. The hydrophobic phase of the composition can help to protect and stabilize the flavor in the tooth whitening product, as the package of the tooth whitening product does not include a barrier layer. Barrier layers, such as aluminum barrier layer or plastic barrier layers (e.g. ethyl vinyl alcohol), are typically incorporated in packages to help stabilize ingredients such as flavors, especially when used to package compositions that are not multi-phase.

Since the package of the present invention is free of a barrier layer, incorporating the flavor in the hydrophobic phase of the composition can help to protect and stabilize the flavor during storage. In this regard, the flavor is preferably dispersed in the hydrophobic phase, and is preferably premixed with other hydrophobic phase component(s) before combining with hydrophilic phase component(s). In one aspect, for example, if the hydrophobic phase comprises petrolatum, the flavor is premixed with the petrolatum before combining with the hydrophilic phase component(s).

Suitable flavors can comprise oil of wintergreen, oil of peppermint, oil of spearmint, clove bud oil, menthol, anethole, methyl salicylate, eucalyptol, 1-menthyl acetate, sage, eugenol, parsley oil, oxanone, alpha-irisone, marjoram, lemon, orange, propenyl guaethol, cinnamon, vanillin, thymol, linalool, cinnamaldehyde glycerol acetal (known as CGA), and mixtures thereof. Preferably, the flavor comprises menthol. The flavor is generally used at levels of from about 0.01% to about 5%, in particular from about 0.1% to about 3%, more particular from about 0.3% to about 2%, by weight of the composition.

The hydrophobic phase can comprise non-toxic edible oils, saturated or unsaturated fatty alcohols, aliphatic hydrocarbons, long chain triglycerides, fatty esters, and mixtures thereof. In certain aspects, the hydrophobic phase may also comprise silicones, polysiloxanes, and mixtures thereof. In certain aspects, the hydrophobic phase may be selected from mineral oil, petrolatum, and mixtures thereof. Preferably the hydrophobic phase comprises petrolatum, e.g. white petrolatum. Examples of petrolatum include Snow White Pet—C from Calumet Specialty Products (Indianapolis, IN) G-2191 from Sonneborn (Parsippany, NJ), G-2218 from Sonneborn, G-1958 from Sonneborn, G-2180 from Sonneborn, Snow White V28 EP from Sonneborn, and Snow White V30 from Sonneborn, and mixtures thereof. Preferably, the hydrophobic phase comprises at least about 30%, at least about 50%, at least about 60%, or at least about 70%, by weight of the hydrophobic phase, of petrolatum.

The multi-phase oral composition of the present invention will typically comprise hydrophobic phase at a level of at least about 30%, at least about 40%, at least about 50%, at least about 60%, at least about 70%, at least about 80%, or at least about 90%, by weight of the multi-phase composition; up to no more than about 99%, no more than about 95%, or no more than about 90%, by weight of the multi-phase oral composition.

The hydrophobic phase will preferably have a cone penetration consistency value within a certain range to provide improved protection and stabilization of the flavor, and release an effective amount of the bleaching agent or active agent during use. The cone penetration consistency value of the hydrophobic phase may be in the range of from about 100 to about 500, preferably in the range from about 150 to about 250, and more preferably in the range of from about 170 to about 200 or any other numerical range, which is narrower and which falls within such broader numerical range, as if such narrower numerical ranges were all expressly written herein, as measured according to ASTM method D937-07. In certain aspects, the cone penetration consistency value of the hydrophobic phase may be from about 10, 25, 50, 100, 110, 120, 130, 140, 150, 160, 170, 180, 190, 200, 210, 220, 230, 240, 250, 300, 400, or 500, to about 25, 50, 100, 110, 120, 130, 140, 150, 160, 170, 180, 190, 200, 210, 220, 230, 240, 250, 300, 400, or 500, or any other numerical range, which is narrower, and which falls within such broader numerical range, as if such narrower numerical ranges were all expressly written herein as measured according to ASTM method D937-07.

Hydrophilic Phase

The hydrophilic phase of the present compositions comprises a peroxide bleaching agent. In one aspect, the hydrophilic phase comprises an aqueous phase comprising the peroxide bleaching agent, preferably hydrogen peroxide. In this aspect, the aqueous phase can comprise hydrogen peroxide at a level of from about 2%, 5%, 8.75%, 10%, 15%, 17.5%, 20%, 25%, 30%, 35%, 45%, 50%, 60%, or 67% to about 67%, 60% to about 50%, 45%, 40%, 35%, 30%, 25%, 20%, 17.5%, 15%, 10%, 8.75%, or 5%, by weight of the aqueous phase, or any other numerical range, which is narrower and which falls within such broader numerical range, as if such narrower numerical ranges were all expressly written herein.

The total level of peroxide bleaching agent in the multi-phase oral composition can be from about 0.001%, 0.01%, 0.02%, 0.03%, 0.04%, 0.05%, 0.06%, 0.07%, 0.08%, 0.09%, 0.095% 0.099995%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15% or 20%, to about 0.1%, 1%, 5%, 10%, 15% or 20%, by weight of the multi-phase oral composition, or any other numerical range, which is narrower and which falls within such broader numerical range, as if such narrower numerical ranges were all expressly written herein.

In one aspect, the composition is an emulsion, preferably a water-in-oil emulsion, wherein the aqueous phase is discontinuous and is dispersed as droplets within the hydrophobic phase, which is continuous. The size of the droplets of the aqueous phase can be a factor in decreasing oral/topical irritation and/or tooth-sensitivity. If the size of the droplets of the aqueous phase is too large it may lead to large spots on oral/topical/tooth surfaces that are exposed to a high concentration of the bleaching agent, which in turn may lead to oral/topical irritation and/or tooth-sensitivity.

In one aspect, the number-average equivalent-diameter or volume-average equivalent-diameter of the droplets of aqueous phase may be from 0.001 micron, 0.01 micron, 0.1 micron, or 1 micron, up to no more than about 0.001 micron, 0.01 micron, 0.1 micron, 1 micron, 5 microns, 10 microns, 50 microns, 100 microns, 500 microns, or 1000 microns or any other numerical range, which is narrower and which falls within such broader numerical range, as if such narrower numerical ranges were all expressly written herein.

Compositions that have a high density of large droplets of aqueous phase may lead to oral/topical irritation and/or tooth-sensitivity. In one aspect, the "two-dimensional density of droplets" of aqueous phase with a cross-sectional area larger than about 1000, 3000, 10000, 20000, or 50000 square microns may be no more than about 0.5, 1, 2, 3, 4, 5, 6, 7, 8, 9, 10, 15, 20, 25, 50, or 100 per square centimeter of the two-dimensional plane, or any other numerical range, which is narrower and which falls within such broader numerical range as if such narrower numerical ranges were all expressly written herein. The procedure to measure the two-dimensional density of droplets is described in detail in US 2018/0133119 A1, which is incorporated by reference herein.

The hydrophilic phase can comprise hydrophilic bleaching agent particles. Examples of suitable hydrophilic bleaching agent particles include urea peroxide, and complexes of hydrogen peroxide and polyvinylpyrrolidone polymers. In one aspect, the hydrophilic bleaching agent particles can constitute the hydrophilic phase itself (i.e. the hydrophilic phase consists of hydrophilic bleaching agent particles). In certain aspects, the hydrophilic bleaching agent particles may be from about 0.6% to about 10%, or from about 0.6% to about 6%, or from about 1% to about 5%, or from about 1% to about 3% by weight of the multi-phase oral composition, or any other numerical range, which is narrower and which falls within such broader numerical range, as if such narrower numerical ranges were all expressly written herein. Multi-phase oral compositions comprising hydrophilic bleaching agent particles suitable for the present invention are described in detail in U.S. application Ser. No. 16/842,800, filed Apr. 8, 2020, which is incorporated by reference herein.

Emulsifier

The multi-phase oral compositions can optionally further comprise an emulsifier. In one aspect, the composition can comprise from about 0.001% to about 30%, by weight of the multi-phase composition, of emulsifier. In certain aspects, the multi-phase oral composition can comprise from about 0 to about 0.1%, from about 0.1% to about 5%, from about 0.1% to about 3%, or from about 0.5% to about 1.5%, by weight of the multi-phase oral composition, of emulsifier. In one aspect, the multi-phase oral composition is free of emulsifier.

Preferred emulsifiers, especially for multi-phase oral compositions in the form of a water-in-oil emulsion, include those having a hydrophilic-lipophilic balance (HLB) value of from about 1 to about 10, an HLB value of from about 3 to about 8, an HLB value from about 4 to about 7, or an HLB from about 4 to about 6.

Suitable emulsifiers can include (i) natural emulsifying agents, such as acacia, gelatin, lecithin and cholesterol; (ii) finely dispersed solids, such as colloidal clays, bentonite, veegum, magnesium aluminum silicate; and (iii) synthetic emulsifying agents, such as salts of fatty acids, sulfates such as sorbitan trioleate, sorbitan tristearate, sucrose distearate, propylene glycol monostearate, glycerol monostearate, propylene glycol monolaurate, sorbitan monostearate, sorbitan monolaurate, polyoxyethylene-4-lauryl ether, sodium lauryl sulfate, sulfonates such as dioctyl sodium sulfosuccinate, glyceryl esters, polyoxyethylene glycol esters and ethers, diethylene glycol monostearate, PEG 200 distearate, and sorbitan fatty acid esters, such as sorbitan monopalmitate, and their polyoxyethylene derivatives, polyoxyethylene glycol esters such as the monostearate, Polysorbate 80 (ethoxylated sorbitan monooleate); and mixtures thereof.

Sweetening Agent

The multi-phase oral composition can optionally further comprise a sweetening agent such as sucralose, sucrose, glucose, saccharin, dextrose, levulose, lactose, mannitol, sorbitol, fructose, maltose, xylitol, saccharin salts, thaumatin, aspartame, D-tryptophan, dihydrochalcones, acesulfame and cyclamate salts, especially sodium cyclamate and sodium saccharin, and mixtures thereof. If present, the composition contains from about 0.1% to about 10% of sweetening agent, in particular from about 0.1% to about 1%, by weight of the composition.

Cone Penetration Consistency Value

The multi-phase oral composition will preferably have a cone penetration consistency value within certain ranges. The cone penetration consistency value of the multi-phase oral composition can be a factor to ensure that the multi-phase oral composition: 1) is substantive and does not run down the teeth or run out of the applicator during application or during use; and 2) releases an effective amount of the bleaching agent or active agent during use. Specifically, if the cone penetration consistency value of the multi-phase oral composition is too high, the multi-phase oral composition may not be substantive and run down the teeth or run out of the delivery carrier during application or during use. In contrast, if the cone penetration consistency value of the multi-phase oral composition is too low, the multi-phase oral composition may not release an effective amount of the bleaching agent or active agent during use, and/or be difficult to dispense from the package of the present invention. In certain aspects, the cone penetration consistency value of the multi-phase oral compositions may be in the range of from about 100 to about 500, preferably in the range from about 150 to about 250, and more preferably in the range of from about 170 to about 200 or any other numerical range, which is narrower and which falls within such broader numerical range, as if such narrower numerical ranges were all expressly written herein, as measured according to ASTM method D937-07. In certain embodiments, the cone penetration consistency value of the multi-phase oral composition may be from about 10, 25, 50, 100, 110, 120, 130, 140, 150, 160, 170, 180, 190, 200, 210, 220, 230, 240, 250, 300, 400, or 500, to about 25, 50, 100, 110, 120, 130, 140, 150, 160, 170, 180, 190, 200, 210, 220, 230, 240, 250, 300, 400, or 500, or any other numerical range, which is narrower, and which falls within such broader numerical range, as if such narrower numerical ranges were all expressly written herein as measured according to ASTM method D937-07.

Suitable multi-phase oral compositions in the form of emulsions, such as water-in-oil emulsions, are described in detail in US 2018/0133119 A1, which is incorporated by reference herein. Suitable multi-phase oral compositions in the form of jammed oil-in-water emulsions are described in detail in U.S. application Ser. Nos. 16/850,033 and 16/850,035, filed Apr. 16, 2020, which are incorporated by reference herein. Suitable multi-phase oral compositions comprising hydrophilic bleaching agent particles are described in detail in U.S. application Ser. No. 16/842,800, filed Apr. 8, 2020, which is incorporated by reference herein.

Optional Applicator Device

The tooth whitening product of the present invention can further be provided with an applicator, which is used to apply the tooth whitening composition to teeth after being dispensed from the package of the present invention. The applicator can be a separate applicator device, such as a wand applicator. A suitable applicator device is described in detail in U.S. application Ser. No. 16/898,469, filed Jun. 11, 2020, which is incorporated by reference herein.

FIG. 1 shows a package 10 of the present invention comprising a container 20 in the form of a tube and having a cap 30.

Figure 2:
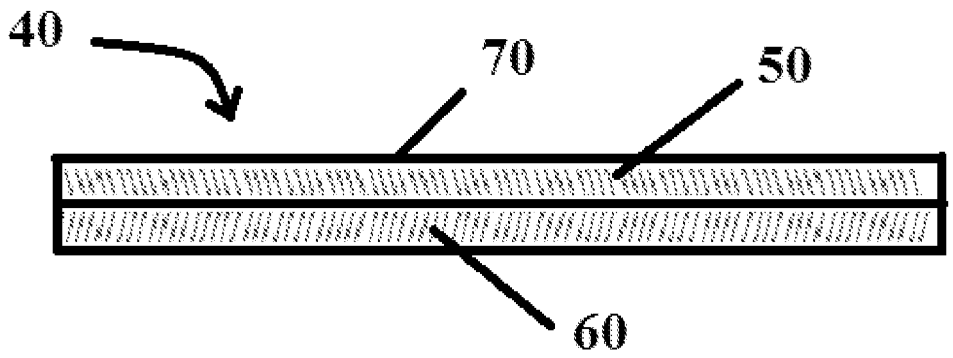
FIG. 2 is a cross-sectional view of an oxygen-permeable substrate of the present invention.

The oxygen-permeable substate 40 used to form the container comprises two layers, which are co-extruded, as shown in FIG. 2. The first layer 50, which faces the external environment, comprises about 50% LDPE, about 50% LLDPE, and a minor amount of colorant. The second layer 60, which faces the tooth whitening composition contained inside the container, comprises about 45% HDPE, about 45% LLDPE, about 10% of polyolefin copolymer, and a minor amount of colorant.

The outer surface 70 of the first layer 50 of the container 20 can be decorated using inks, metallic hot stamping foil, and/or matte or gloss varnishes (not shown).

The oxygen transmission rate of a sample of the oxygen-permeable substrate 40 is measured according to ASTM D3985 using an Oxtran 2/21 Oxygen Permeability Instrument available from MOCON Laboratory (Minneapolis, Minnesota, USA), with the following results:

| Oxygen Transmission Rate | | Steady State or |
|---|---|---|
| Replicate | cc/($m^2$*day) | Test Duration* |
| A | 237 | Steady State |
| B | 242 | Steady State |

* The maximum test duration is 120 hours.

The use of such a package 10 for containing a multi-phase oral composition of the present invention comprising a peroxide bleaching agent results in a tooth whitening product that does not suffer from undesirable expansion of the package during storage of the tooth whitening product over time.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A tooth whitening product comprising:
- a multi-phase oral composition comprising:
  - a hydrophobic phase comprising a flavor; and
  - a hydrophilic phase comprising a peroxide bleaching agent; and
- a package comprising:
  - a container formed of an oxygen-permeable substrate comprising a first layer and a second layer, wherein the first layer comprises a blend of low density polyethylene and linear low density polyethylene, and the second layer comprises a blend of high density polyethylene and linear low density polyethylene, wherein the substrate has an oxygen transmission rate at 23° C. of at least about 5 cc/(m2*day);
  - a dispensing orifice in fluid communication with the container; and
- a cap covering the dispensing orifice;
- wherein the oxygen-permeable substrate of the container is free of a barrier layer;

wherein the multi-phase oral composition is contained in the package.

2. The tooth whitening product of claim 1, wherein the oxygen-permeable substrate has an oxygen transmission rate at 23° C. of at least about 10 cc/(m2*day).

3. The tooth whitening product of claim 2, wherein the oxygen transmission rate at 23° C. is at least about 20 cc/(m2*day).

4. The tooth whitening product of claim 3, wherein the oxygen transmission rate at 23° C. is at least about 50 cc/(m2*day).

5. The tooth whitening product of claim 1, wherein the barrier layer has an oxygen transmission rate of less than about 5 cc/(m2*day).

6. The tooth whitening product of claim 5, wherein the oxygen transmission rate is less than about 1 cc/(m2*day).

7. The tooth whitening product of claim 1, wherein the hydrophilic phase comprises an aqueous phase or hydrophilic peroxide bleaching agent particles.

8. The tooth whitening product of claim 1, wherein the multi-phase oral composition is an emulsion.

9. The tooth whitening product of claim 1, wherein the hydrophilic phase is an aqueous phase.

10. The tooth whitening product of claim 9, wherein the aqueous phase comprises at least about 10%, by weight of the aqueous phase, of peroxide bleaching agent, and wherein the multi-phase oral composition comprises less than about 10%, by weight of the multi-phase oral composition, of peroxide bleaching agent.

11. The tooth whitening product of claim 9, wherein the aqueous phase comprises at least about 20%, by weight of the aqueous phase, of peroxide bleaching agent, and wherein the multi-phase oral composition comprises less than about 5%, by weight of the multi-phase oral composition, of peroxide bleaching agent.

12. The tooth whitening product of claim 1, wherein the hydrophilic phase further comprises sweetener.

13. The tooth whitening product of claim 1, wherein the multi-phase oral composition is a water-in-oil emulsion, wherein the hydrophilic phase is dispersed as droplets within the hydrophobic phase.

14. The tooth whitening product of claim 1, wherein the multi-phase oral composition comprises at least about 50%, by weight of the multi-phase oral composition, of hydrophobic phase.

15. The tooth whitening product of claim 1, wherein the hydrophobic phase comprises non-toxic edible oils, saturated or unsaturated fatty alcohols, aliphatic hydrocarbons, long chain triglycerides, fatty esters, silicones, polysiloxanes, mineral oil, petrolatum, or mixtures thereof.

16. The tooth whitening product of claim 1, wherein the flavor is dispersed within the hydrophobic phase.

17. The tooth whitening product of claim 1, wherein the flavor is premixed with other hydrophobic phase component(s) before combining with hydrophilic phase component(s).

18. The tooth whitening product of claim 1, wherein the hydrophobic phase comprises petrolatum.

19. The tooth whitening product of claim 18, wherein the flavor is premixed with petrolatum.

20. The tooth whitening product of claim 1, wherein the multi-phase oral composition has a cone penetration consistency value of from about 10 to about 500.

21. The tooth whitening product of claim 20, wherein the cone penetration consistency value is from about 100 to about 300.

22. The tooth whitening product of claim 1, wherein the first layer blend is about 50% by weight low density polyethylene and about 50% by weight linear low density polyethylene.

23. The tooth whitening product of claim 1, wherein the second layer blend comprises about 45% by weight high density polyethylene and about 45% by weight linear low density polyethylene.

24. The tooth whitening product of claim 23, wherein the second layer blend further comprises about 10% by weight polyolefin copolymer.

* * * * *